US005554150A

United States Patent [19]

Bousseau et al.

[11] Patent Number: 5,554,150

[45] Date of Patent: Sep. 10, 1996

[54] GRANULOCYTE COLONY-STIMULATING FACTOR SOLUTION DELIVERY METHOD

[75] Inventors: Anne Bousseau, Paris; Armand Frydman, Verriéres-le-Buisson; Jean-Paul Plard, Vitry; Gilles Spenlehauer, Cachan; Michel Veillard, Sceaux, all of France

[73] Assignee: Rhone-Poulenc Rorer S.A., Antony Cedex, France

[21] Appl. No.: 373,287

[22] PCT Filed: Jul. 19, 1993

[86] PCT No.: PCT/FR93/00731

§ 371 Date: Jan. 20, 1995

§ 102(e) Date: Jan. 20, 1995

[87] PCT Pub. No.: WO94/02164

PCT Pub. Date: Feb. 3, 1994

[30] Foreign Application Priority Data

Jul. 23, 1992 [FR] France .................................. 92 09079

[51] Int. Cl.$^{6}$ ..................................................... A61K 9/22

[52] U.S. Cl. .................................... 604/891.1; 604/892.1; 604/49

[58] Field of Search .................................. 604/892.1, 49, 604/891.2, 890.1; 424/85.2, 85.1; 514/8; 548/218

[56] References Cited

U.S. PATENT DOCUMENTS

| | | |
|---|---|---|
| 5,186,931 | 2/1993 | Kishimoto et al. . |
| 5,202,117 | 4/1993 | Tsuji et al. . |
| 5,241,072 | 8/1993 | Colon et al. . |
| 5,324,280 | 6/1994 | Wong et al. . |
| 5,416,071 | 5/1995 | Igari et al. . |

*Primary Examiner*—Randall L. Green
*Assistant Examiner*—Perry E. Van Over

[57] ABSTRACT

Methods and devices for delivery of granulocyte-colony stimulating factor to a patient are disclosed. The method comprises continuous subcutaneous delivery of a solution comprising granulocyte-colony stimulating factor to the patient. Devices for continuous administration are also disclosed.

19 Claims, No Drawings

GRANULOCYTE COLONY-STIMULATING FACTOR SOLUTION DELIVERY METHOD

The present invention relates to a new method for the delivery of solutions containing a granulocyte-colony stimulating factor. In particular, this invention relates to a process for the delivery of aqueous G-CSF solutions.

The chemotherapy frequently used in the treatment of cancers causes the destruction of cancerous cells but also often has clinical side-effects related to this treatment. Thus, during these treatments, the existence is apparent of infectious diseases due to microorganisms which are resistant to any antibiotic therapy. In addition, during these chemotherapeutic treatments, part of the natural defences of living organisms is destroyed, which explains the appearance of infectious diseases in these organisms.

In order to avoid as far as possible the appearance of these infectious diseases related to chemotherapy, it has been proposed to use a substance which activates the natural defence abilities of the organism. In each organism, there exist defence systems which, in man, largely consist of leucocytes. These leucocytes provide for phagocytosis of the infectious agents or participate in their destruction and consequently prevent multiplication of harmful microorganisms within the sick organism. Granulocyte-colony stimulating factor has recently appeared among substances which promote proliferation or multiplication of leucocytes. This factor has been protected in the European patent application published for example under the number EP 237,545.

This granulocyte-colony stimulating factor is delivered to man or to animals at very low doses, of the order of 0.1 to 500 μg for an adult man. The delivery of such low doses poses a problem of dilution of the active principle which had to be overcome. In fact, this active principle, which is a polypeptide, has the disadvantage of being adsorbed on the walls of the containers with which it has been brought into contact, whether syringes or perfusion bottles. The problem related to this adsorption was solved in the British patent application published under the number GB 2,193,631.

It is known, for example, according to this British patent application, that it is possible to stabilize the granulocyte-colony stimulating factor solution by addition to the aqueous solution of a protein which is competitive as regards adsorption on the walls of the container, which protein consists, for example, of albumin, and of a polysaccharide coupled to a non-ionic surfactant agent.

These solutions, when they are delivered to animals subcutaneously, cause, only two days after injection, an increase of five times the amount of polynucleate neutrophiles, but this increase is reduced to approximately two times the normal eight days after injection, all this being evaluated with respect to untreated controls.

A method of delivery using particles having a prolonged release was proposed in Patent Application EP 263,490. This method makes it possible, by virtue of the delivery of polymeric particles based on a poly-(lactic acid) polymer or on a copolymer of lactic acid and of glycolic acid containing the granulocyte-colony stimulating factor, to avoid the daily delivery of aqueous solutions of this said factor. These particles make it possible to obtain an effect virtually equivalent to that obtained with a daily subcutaneous injection of aqueous solutions of the said factor. The maximum effect is thus maintained throughout the period of release of the microparticles, which can reach two weeks.

It appeared, in an entirely surprising way, that when the aqueous stimulating factor solution was continuously introduced subcutaneously in animals or in man, the multiplier effect on the neutrophile content was greatly increased. In contrast, it appeared that the same dose injected cutaneously in a single daily injection, led to an increase six times less than that caused by the delivery of the same daily dose continuously. This entirely surprising effect has an entirely favourable consequence for the treatment using this type of active principle. It thus makes it possible, for the same therapeutic effect, that is to say for the same increase in blood neutrophile level, to decrease the doses injected by at least a factor of ten and still more advantageously by a factor of twenty.

The present invention thus consists in injecting the solutions described in the British patent published under the number GB 2,163,631. These solutions preferably have the following composition:

| | |
|---|---|
| granulocyte-colony stimulating factor | 250 μg |
| serum albumin | 1 mg |
| non-ionic surface-active agent | 0.1 mg |
| saccharide | 50 mg |
| disodium phosphate | 0.8 mg |
| monosodium phosphate | 3.6 mg |
| sodium chloride | 3.1 mg |
| water | 660 mg |

The surface-active agent used is preferably polysorbate 80. The saccharide used is preferably mannitol. It is clearly understood that the composition is not strictly confined to the quantitative distribution mentioned but that it can vary in concentration within wide limits; the volume injected will be inversely proportional to the concentration of the solution.

For an optimum response, it is advised to deliver a dose of between 0.05 and 2 μg/kg/h. This delivery can be carried out in practice using a pump implanted in the subcutaneous tissue or using an implant which makes possible continuous and steady release of the active principle.

The present invention is more completely described using the following examples which should not be regarded as being limiting of the invention.

EXAMPLE

Experimental conditions

1) Equipment

Use is made of Alzet osmotic minipumps having a capacity of 200 μl, filled with a sufficient amount of active principle to make possible steady and constant release for 8 days, at the rate of 1 μl/hour of stimulating factor solution, i.e. 10 μg/24H/animal.

2) Animals

Use is made of 40 rats (20 males and 20 females) aged from 7 to 8 weeks and weighing from 180 to 200 g Active principle: lyophilisate containing 250 μg of stimulating factor dissolved in 0.66 ml of sterile water for injections Equipment: Alzet osmotic pumps filled with a sufficient amount of active principle to enable release of the stimulating factor for eight days at the rate of 10 μg/24 H per animal.

The forty animals involved in the test are thus distributed:

A—10 are controls which receive only one daily (8 days) subcutaneous injection of a sodium chloride solution.

B—10 are operating technique controls, on which a dorsoscapular incision is made, without introduction of minipump, with suture.

C—10 others receive a daily subcutaneous injection, of 24 μl/day, of stimulating factor solution for 8 days.

D—the last ten receive a subcutaneous implantation, in the dorsoscapular region, of an Alzet minipump which delivers 1 μl/H of stimulating factor solution for 8 days.

The results of the neutropoiesis are shown in Tables 1 and 2.

TABLE 1

| | NEUTROPOIESIS | | | | |
|---|---|---|---|---|---|
| | Number of Neutrophiles/mm³ | | | | |
| MALES | T0 | 2D | 3D | 5D | 8D |
| A | 800(350)* | 1900(1300) | 3700(3000) | 5500(2300) | 3500(1100) |
| B | 1600(600) | 2450(700) | 2400(1200) | 4200(2400) | 3560(1300) |
| C | 1200(650) | 8500(4500) | 7050(2500) | 3300(3800) | 7500(1700) |
| D | 1800(800) | 17000(3400) | 26000(5600) | 26600(7800) | 48500(20000) |

*represents the standard deviation

TABLE 2

| | NEUTROPOIESIS | | | | |
|---|---|---|---|---|---|
| | Number of Neutrophiles/mm³ | | | | |
| FEMALES | T0 | 2D | 3D | 5D | 8D |
| A | 460(400) | 1900(800) | 1600(600) | 1800(600) | 1500(700) |
| B | 890(400) | 1100(600) | 2500(1400) | 1900(800) | 2350(1200) |
| C | 500(300) | 6600(3000) | 7400(1900) | 4100(2000) | 5000(1700) |
| D | 1100(400) | 18000(3000) | 31000(10000) | 26000(7200) | 46000(10000) |

The same test as in the preceding example was carried out with less concentrated stimulating factor solutions; concentrations of 0.3 μg/24 H (batch D1), 1 μg/24 H (batch D2) and 3 μg/24H (batch D3) were tested on similar animals and under the same conditions as in the preceding example. The results of the neutropoiesis are shown in Table 3.

TABLE 3

| | NEUTROPOIESIS | | | |
|---|---|---|---|---|
| | Number of Neutrophiles/mm³ | | | |
| Groups | T0 | 3D | 5D | 8D |
| A | 1800(400) | 2000(800) | 2000(700) | 2200(500) |
| B | 2700(2400) | 2700(700) | 3200(1000) | 2700(1300) |
| D1 | 1500(1300) | 5800(800) | 4900(1600) | 5400(1800) |
| D2 | 1200(700) | 10300(4500) | 10100(5100) | 18700(4400) |
| D3 | 1600(500) | 11000(4000) | 8500(4000) | 30000(7100) |

We claim:

1. A method for administering granulocyte-colony stimulating factor to a patient comprising continuous subcutaneous delivery of a solution comprising granulocyte-colony stimulating factor to said patient.

2. The method of claim 1, wherein said delivery is from a device containing said solution.

3. The method of claim 2, wherein said device is implantable.

4. The method of claim 3, wherein said device is a pump.

5. The method of claim 4, wherein said pump is an osmotic pump.

6. The method of claim 1, wherein said granulocyte-colony stimulating factor is administered in a dose of between 0.05 and 2 μg/kg/h.

7. The method of claim 6, wherein said dose is between 0.3 and 10 μg/24h.

8. The method of claim 1, wherein said solution comprises granulocyte-colony stimulating factor, serum albumin, a non-ionic surface-active agent, a saccharide, disodium phosphate, monosodium phosphate, sodium chloride and water.

9. The method of claim 8, wherein said non-ionic surface-active agent is polysorbate 80.

10. The method of claim 8, wherein said saccharide is mannitol.

11. A device containing a solution comprising granulocyte-colony stimulating factor and capable of continuous subcutaneous delivery of said solution to a patient.

12. The device of claim 11, wherein said device is implantable.

13. The device of claim 12, wherein said device is a pump.

14. The device of claim 13, wherein said pump is an osmotic pump.

15. The device of claim 11, wherein said granulocyte-colony stimulating factor is administered in a dose of between 0.05 and 2 μg/kg/h.

16. The device of claim 15, wherein said dose is between 0.3 and 10 μg/24h.

17. The device of claim 11, wherein said solution comprises granulocyte-colony stimulating factor, serum albumin, a non-ionic surface-active agent, a saccharide, disodium phosphate, monosodium phosphate, sodium chloride and water.

18. The device of claim 17, wherein said non-ionic surface-active agent is polysorbate 80.

19. The device of claim 17, wherein said saccharide is mannitol.

* * * * *